(12) United States Patent
Osborne (10) Patent No.: US 11,332,775 B2
(45) Date of Patent: May 17, 2022

(54) METHOD FOR NORMALIZING A NUCLEIC ACID SAMPLE

(71) Applicant: Agency for Science, Technology and Research, Singapore (SG)

(72) Inventor: Robert Osborne, Saffron Walden (GB)

(73) Assignee: **AGENCY FOR SCIENCE, TECHNOLOGY AND RESEARCH ("A*STAR")**, Singapore (SG)

( * ) Notice: Subject to any disclaimer, the term of this patent is extended or adjusted under 35 U.S.C. 154(b) by 539 days.

(21) Appl. No.: 16/479,124

(22) PCT Filed: Jan. 10, 2018

(86) PCT No.: PCT/IB2018/050137
§ 371 (c)(1),
(2) Date: Jul. 18, 2019

(87) PCT Pub. No.: WO2018/134700
PCT Pub. Date: Jul. 26, 2018

(65) Prior Publication Data
US 2019/0390254 A1 Dec. 26, 2019

(30) Foreign Application Priority Data

Jan. 19, 2017 (GB) .................................. 1700941

(51) Int. Cl.
| | |
|---|---|
| C12Q 1/6806 | (2018.01) |
| C12N 9/22 | (2006.01) |
| C12N 15/10 | (2006.01) |
| C12N 15/11 | (2006.01) |
| C12Q 1/6876 | (2018.01) |

(52) U.S. Cl.
CPC ............ *C12Q 1/6806* (2013.01); *C12N 9/22* (2013.01); *C12N 15/1068* (2013.01); *C12N 15/11* (2013.01); *C12Q 1/6876* (2013.01); *C12N 2310/20* (2017.05); *C12N 2800/80* (2013.01); *C12Q 2600/166* (2013.01)

(58) Field of Classification Search
None
See application file for complete search history.

(56) References Cited

U.S. PATENT DOCUMENTS

2014/0356867 A1  12/2014  Peter et al.

FOREIGN PATENT DOCUMENTS

| WO | WO 1999/002727 | 1/1999 |
|---|---|---|
| WO | WO 2013/003489 | 1/2013 |
| WO | WO 2015/066695 | 5/2015 |
| WO | WO 2016/025872 | 2/2016 |
| WO | WO 2016/100955 | 6/2016 |

OTHER PUBLICATIONS

Anders, et al.; "In vitro Enzymology of Cas9"; Methods Enzymol.; vol. 546, pp. 1-20 (2014).
Farasat, et al.; "A Biophysical Model of CRISPR/Cas9 Activity for Rational Design of Genome Editing and Gene Regulation"; PLoS; 33 pages (Jan. 29, 2016).
Gong, et al.; "DNA unwinding is the primary determinant of CRISPR-Cas9 activity"; bioRxiv; 36 pages (Oct. 19, 2017).
Hu, et al.; "Chemical Biology Approaches to Genome Editing: Understanding, Controlling, and Delivering Programmable Nucleases"; Cell Chemical Biology; vol. 23, pp. 57-73 (Jan. 21, 2016).
Jinek, et al.; "A programmable dual RNA-guided DNA endonuclease in adaptive bacterial immunity"; Science; vol. 337, No. 6096, pp. 816-821 (Aug. 17, 2012).
Josephs, et al.; "Structure and specificity of the RNA-guided endonuclease Cas9 during DNA interrogation, target binding and cleavage"; Nucleic Acids Research; vol. 43, No. 18, pp. 8924-8941 (2015).
Ma, et al.; "CRISPR-Cas9 nuclear dynamics and target recognition in living cells"; J. Cell Biol; vol. 214, No. 5, pp. 529-537 (2016).
Shvets, et al.; "Mechanism of Genome Interrogation: How CRISPR RNA-Guided Cas9 Proteins Locate Specific Targets on DNA"; Biophysical Journal; vol. 113, pp. 1416-1424 (Oct. 3, 2017).
Sternberg, et al.; "DNA interrogation by the CRISPR RNA-guided endonuclease Cas9"; Nature; vol. 507, 17 pages (Mar. 6, 2014).
Suzuki, et al.; "In vivo genome editing via CRISPR/Cas9 mediated homology-independent targeted integration"; Nature; vol. 540, No. 7631, pp. 144-149 (Dec. 1, 2016).
Wang, et al.; "CRISPR/Cas9 in Genome Editing and Beyond"; Annu. Rev. Biochem.; vol. 85, pp. 227-264 (2016).
Yang, et al.; "Basement membrane stiffening promotes retinal endothelial activation associated with diabetes"; The FASEB Journal; pp. 601-611 (2016).

*Primary Examiner* — Kaijiang Zhang
(74) *Attorney, Agent, or Firm* — James S. Keddie; Bozicevic, Field & Francis LLP (57) ABSTRACT

Among other things, a method for normalizing a sample is provided. In some embodiments, the method comprises: (a) reacting a sample with a limiting amount of a single-turnover sequence-specific endonuclease that recognizes a target sequence, thereby cleaving a portion of the nucleic acid molecules that comprise the target sequence and producing a normalized amount of a first cleavage product; and (b) isolating, transcribing or selectively amplifying the normalized amount of the first cleavage product. In this method, because a limiting amount of the endonuclease is used, the normalized amount of the first cleavage product is determined by the limiting amount of the first single-turnover sequence-specific endonuclease used in step (a).

20 Claims, 1 Drawing Sheet

METHOD FOR NORMALIZING A NUCLEIC ACID SAMPLE

CROSS-REFERENCE TO RELATED APPLICATIONS

This application is a § 371 national phase of International Application No. PCT/IB2018/050137, filed on Jan. 10, 2018, which claims the benefit of United Kingdom Patent Application No. 1700941.6, filed on Jan. 19, 2017, which applications are incorporated by reference herein.

BACKGROUND

Many molecular protocols, e.g., sequencing library preparation, fragmentation, adaptor ligation, tagmentation, etc. require samples that are at a concentration that is within an acceptable working range. In the laboratory, this is typically accomplished by measuring the concentration of nucleic acid in a sample and then only using an appropriate amount of the sample (an aliquot or dilution of the same) in the next step of the protocol. This process is referred to as "normalization" and results in the generation of samples that have substantially equal amounts of nucleic acid molecules in them. In many cases, samples are normalized prior to pooling, to ensure that the same amount of each sample is processed in the next step of the method.

Conventional normalization methods involve physically measuring the amount of nucleic acid in the sample, performing a calculation, and then making an appropriate adjustment to the sample. Such methods are generally time consuming, labor intensive, and prone to human error. In addition, some methods require sacrificing some of the sample, denaturing the sample and/or specialized laboratory equipment. In many cases (particularly in a high-throughput laboratory) the normalization step is rate limiting because it cannot be automated.

Better sample normalization methods are therefore needed.

SUMMARY

Various methods for normalizing a sample are provided. In some embodiments, the method comprises: (a) reacting a sample with a limiting amount of a single-turnover sequence-specific endonuclease that recognizes a target sequence, thereby cleaving a portion of the nucleic acid molecules that comprise the target sequence and producing a normalized amount of a first cleavage product; and (b) isolating, transcribing or selectively amplifying the normalized amount of the first cleavage product. In this method, because a limiting amount of the endonuclease is used, the normalized amount of the first cleavage product is determined by the limiting amount of the first single-turnover sequence-specific endonuclease used in step (a). In performing the method, the amount of the cleavage product (which may contain a sequence of interest) can be increased or decreased in direct proportion with the amount of the endonuclease used. For example, if the amount of endonuclease in the reaction doubles, then the amount of product should double (assuming, of course, an excess of starting material exists).

The method finds particular use in normalizing the amount of two or more nucleic acids (e.g., genes or amplification products, etc.) within a sample or between samples. Specifically, as will be discussed in greater detail below, a single sample may be reacted with limiting amounts of two or more single-turnover sequence-specific endonucleases that recognize different target sequences. In these embodiments, the relative amounts of the different cleavage products produced should be proportional to the relative amounts of the endonucleases in the reaction. For example, if one wanted to produce two cleavage products that have a molar ratio of 1:1, the same limiting amount of the two or more single-turnover sequence-specific endonucleases could be used. In another example, two or more different samples can be reacted with the same single-turnover sequence-specific endonuclease. In these embodiments, the relative amount of the cleavage products produced in the reactions should be proportional to the relative amounts of the endonuclease used in the reactions. In this example, if one wanted to produce the same molar amount of cleavage product from two different reactions, the same limiting amount of the single-turnover sequence-specific endonuclease could be used in the reactions.

Other normalization methods (e.g., methods that involve measuring the amount of the nucleic acid in the sample prior to performing a reaction, or methods that involve hybridization of a sample to a limiting amount of an oligonucleotide) are labor intensive, require capital equipment, often require denaturation of the sample, and/or are not accurate. As such, the present method is believed to be a significant contribution to the art. Moreover, the present method can be used to normalize the amounts of specific sequences within a sample (not just between samples). As such, the present method finds particular use in methods in which multiple sequences (e.g., multiple loci or amplification products, etc.) from a single sample need to be normalized prior to analysis.

The sample used in the present normalization method or the product of the present normalization method can be used without quantifying the exact amount of nucleic acid in the sample, e.g., using fluorometry or densitometry, although the sample or the product may be checked to determine whether it contains nucleic acid. In addition, because the endonuclease is sequence-specific, the method can be used to enrich for a particular sequence (e.g., a particular locus). As such, in some embodiments, the method normalizes and enriches for a particular sequence (e.g., a particular locus) in the sample.

Other implementations, embodiments and advantages may be apparent from the description that follows below.

BRIEF DESCRIPTION OF THE DRAWINGS

The skilled artisan will understand that the drawings, described below, are for illustration purposes only. The drawings are not intended to limit the scope of the present teachings in any way.

FIG. 1 schematically illustrates an example of the present method in which two amplicons represented by thick and think lines are normalized in four samples. In this example, biotin is represented by white circles and the bottom of the wells is coated with streptavidin. As shown, the numbers of molecules of the amplicons in the initial samples varies. As shown at the top of the figure, double-stranded amplicons are bound to a streptavidin coated plate via 5' biotin. As shown, the four wells have different numbers of molecules of the thick and thin amplicons. In the next step, the tethered amplicons are reacted with a single turnover, sequence specific endonucleases (e.g., Cas9-RNAs) that are specifically designed to recognize the thick and thin amplicons. In this example, one molecule of a single turnover, sequence specific endonuclease that recognizes the thin amplicon and two molecule of a single turnover, sequence specific endonuclease that recognizes the thick amplicons are added to each well and reactions allowed to go to completion. Next, the cleavage products are isolated. In the method shown, the supernatants are removed to a new plate. Reactions are normalized and the desired concentration of thick/thin amplicons is attained. In the example shown, each normalized sample contains the same number of molecules, and each sample contains exactly one thin amplicon and two thick amplicons.

DEFINITIONS

Before the present subject invention is described further, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antibody" includes a plurality of such antibodies and reference to "a framework region" includes reference to one or more framework regions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "sample" refers to a sample of nucleic acid from a biological source. A sample may be from an animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

"Genetic locus", "locus", "gene" or "locus of interest" in reference to a genome or target polynucleotide, means a contiguous sub-region or segment of the genome or target polynucleotide. As used herein, genetic locus, gene, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it.

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "adaptor" refers to a sequence that is added (e.g., by ligation) to a nucleic acid. An adaptor may be from 5 to 100 or more bases in length, and may provide, e.g., an amplification primer binding site, a sequencing primer binding site, and/or a molecular barcode such as a sample identifier sequence or molecule identifier sequence. An adaptor may be added to the 5' end, the 3' end, or both ends of the nucleic acid molecule. Double stranded adaptors contain a double stranded end that is ligated to a nucleic acid. An adaptor can have an overhang or may be blunt. As will be described in greater detail below, a double stranded adaptor can be added to a fragment by ligating only one strand of the adaptor to the fragment. Y-adaptors and loop adaptors are type of double-stranded adaptors.

The term "sample identifier sequence", "sample index", "multiplex identifier" or "MID" is a sequence of nucleotides that is appended to a target polynucleotide, where the sequence identifies the source of the target polynucleotide (i.e., the sample from which sample the target polynucleotide is derived). In use, each sample can be tagged with a different sample identifier sequence (e.g., one sequence is appended to each sample, where the different samples are appended to different sequences), and the tagged samples can be pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide. When a polynucleotide has a sample identifier sequence at both ends, together, the 3' and 5' sample identifier sequences can identify the sample. In many examples, the sample identifier sequence is only a subset of the bases which are appended to a target oligonucleotide.

The term "molecule identifier sequence" (which may also be referred to as a "counter sequence", or "index" in some instances) is a sequence of nucleotides that can be appended to the nucleic acid fragments of a sample such that the appended sequence of nucleotides, alone or in combination with other features of the fragments, e.g., their fragmentation breakpoints, can be used to distinguish between the different fragment molecules in the sample or a portion thereof. The complexity of a population of molecule identifier sequences used in any one implementation may vary depending on a variety of parameters, e.g., the number of fragments in a sample and/or the amount of the sample that is used in a subsequent step. For example, in certain cases, the molecule identifier sequence may be of low complexity (e.g., may be composed of a mixture of 8 to 1024 sequences). In other cases, the molecule identifier sequence may be of high complexity (e.g., may be composed of 1025 to 1M or more sequences). In certain embodiments, a population of molecule identifier sequences may comprise a degenerate base region (DBR) comprising one or more (e.g., at least 2, at least 3, at least 4, at least 5, or 5 to 30 or more) nucleotides selected from R, Y, S, W, K, M, B, D, H, V, N (as defined by the IUPAC code), or a variant thereof. In some embodiments, a population of molecule identifier sequences may be made by mixing oligonucleotides of a defined sequence together. In these embodiments, the molecule identifier sequence in each of the oligonucleotides may be error correctable. In the methods described herein, the molecule identifier sequence may be used to distinguish between the different fragments in a portion of an initial sample, where the portion has been removed from the initial sample. The molecule identifier sequences may be used in conjunction with other features of the fragments (e.g., the end sequences of the fragments, which define the breakpoints) to distinguish between the fragments. Molecule identifier sequences are described in (Casbon Nuc. Acids Res. 2011, 22 e81) and have been demonstrated to increase the sensitivity of minority variant detection in HIV (Jabara et al 2011), Pap smears (Kinde et al 2013) and RNA-Seq (Shiroguchi et al 2012). The term "minority variant" is defined as a variant that is present in a frequency of less than 20%, relative to other molecules in the sample. In some cases, a minority variant may be a first allele of a polymorphic target sequence, where, in a sample, the ratio of molecules that contain the first allele of the polymorphic target sequence compared to molecules that contain other alleles of the polymorphic target sequence is 1:10 or less, 1:100 or less, 1:1,000 or less, 1: 10,000 or less, 1:100,000 or less or 1:1M or less. Minority variants of drug resistant HIV are described in Gianella et al (J Infect Dis. (2010) 202: 657-666).

The term "defined amount" may be measured in moles, weight or volume if a volume contains a known concentration of nucleic acid. The concentration of nucleic acid in a sample can be determined using any suitable method.

The term "amplifying" is intended to refer to both isothermal amplification methods and methods that require thermocycling (e.g., PCR). Amplification requires increasing the relative concentration of one or more sequences in a sample at least 10-fold, relative to unamplified components of the sample.

The term "nucleic acid template" is intended to refer to the initial nucleic acid molecule that is copied during amplification.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, and Roche, etc. Next-generation sequencing methods may also include nanopore sequencing methods such as commercialized by Oxford Nanopore or electronic-detection based methods such as Ion Torrent technology commercialized by Life Technologies or fluorescent base cleaving methods such as commercialized by Pacific Biosciences.

The terms "reacting" and "treating" are intended to refer to contacting a product (e.g., DNA) with a reagent (e.g., an enzyme), under conditions suitable for the reagent to cause a change in (e.g., fragment or cleave) the product.

The term "unknown amount" refers to an amount that has not been measured or quantified. For example, in some embodiments a sample may contain an unknown amount of nucleic acid. In other embodiments a sample may contain an unknown amount of nucleic acid, although a range of values is known (e.g., after 10 rounds of linear extension a sample has between 1× and 11× the original concentration). In these embodiments, the concentration of the nucleic acid in the sample has not been measured.

The term "nucleic acid" refers to double-stranded DNA, single-stranded DNA, RNA, or any combination thereof. Types of sample that contain nucleic acid include samples that comprise non-amplified nucleic acid and samples that comprise amplified nucleic acid, e.g., PCR amplification products (including RT-PCR and multiplex PCR products) as well as isothermal amplification products.

The terms "tagmentation" and "tagmenting" refer to the simultaneous transposase-catalyzed fragmentation and tagging of a double-stranded DNA sample, as described by, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold under the tradename NEXTERA™ by Illumina (San Diego, Calif.).

The term "single-turnover endonuclease" refers to an endonuclease that cleaves no more than a single molecule of substrate. Specifically, a single molecule of a single turnover endonuclease (which may be a complex comprising a single molecule of protein and a guide nucleic acid) reacts with and cleaves a single molecule of substrate to produce, e.g., two molecules of product. After cleaving one molecule of substrate, such enzymes do not move on to and cleave another substrate molecule. A reaction that contains a single turnover enzyme will stop when all of the single-turnover enzyme has been used once.

The term "sequence-specific endonuclease," refers to an endonuclease that cleaves at (e.g., within or proximal to) a specific sequence that is referred to herein as a "target sequence."

The term "cleaving" refers to a reaction in which one or more phosphodiester bonds are broken in a nucleic acid. A phosphodiester bond in one strand or phosphodiester bonds in both strands broken in a cleavage reaction. Such a reaction could result in a nick or two fragments, for example.

The term "limiting amount" refers to an amount that limits the amount of product that can be formed. In a reaction that contains a limiting amount of a single-turnover enzyme, after a sufficient incubation time the amount of product produced should be directly proportional to the amount of single-turnover enzyme that is in the reaction. For example, if a reaction contains a limiting amount of 1,000 molecules of a single-turnover endonuclease, then the reaction will produce 1,000 molecules of a cleavage product (assuming that the reaction is 100% efficient). Cleavage reactions that contain a limiting amount of an endonuclease can reach equilibrium very rapidly, e.g., within 10 minutes or within 5 minutes. In such reactions, the target sites for the endonuclease are in excess relative to the endonuclease. For example, in some cases, there are at least 2, at least 5, at least 10, at least 100, at least 1,000 or at least 10,000 more target sites for the endonuclease relative to the number of molecules of endonuclease. In any embodiment, a reaction mix that contains a limiting amount of a single-turnover endonuclease may contain less than 1 µmol of the single-turnover endonuclease (i.e., less than $6\times10^{11}$ molecules of the endonuclease), although an amount outside of this range (e.g., less than 1 fmol of the enzyme, i.e., $6\times10^{8}$ molecules of the enzyme) can be used in many cases. In any embodiment, such a reaction mix may contain 1 amol to 100 fmol, 1 amol to 10 fmol, 1 amol to 1 fmol or 1 amol to 100 amol of the endonuclease (i.e., $6\times10^{5}$ to $6\times10^{10}$, $6\times10^{5}$ to $6\times10^{9}$, $6\times10^{5}$ to $6\times10^{8}$, $6\times10^{5}$ to $6\times10^{7}$ molecules of the enzyme). In any embodiment, the concentration of the single turnover endonuclease may be in the range of 1 amol/µl to 100 fmol/µl, e.g., 1 amol/µl to 100 fmol/µl. In some cases, a reaction mix may contain limiting amounts of a plurality of single-turnover endonucleases.

The term "portion" means some but not all. A portion can be less then 50%, less than 20%, less than 10% or less than 5%, for example.

The term "normalized sample" refers to a sample that has a desired amount of nucleic acid molecules. The number and concentration of nucleic acid molecules in a normalized sample is approximately known (e.g., within a range of, e.g., +/−50%, +/−30%, +/−20% or +/−10% of a defined number or concentration). Two samples that are normalized have the approximately the same number or concentration (e.g., within a range of, e.g., +/−50%, +/−30%, +/−20% or +/−10% of a defined number or concentration) of nucleic acid molecules. A sample that contains two or more nucleic acid species that are normalized has two or more nucleic acid species that are at a pre-determined molar ratio. For example, such a sample can contain approximately the same number of molecules of the two or more nucleic acid species.

The term "isolating" refers to the process of separating something in a mixture from other things in that mixture. For example, nucleic acids that are in solution in a container can be isolated from nucleic acids that are attached to a solid support in the container by removing the solution (which contains the nucleic acids that are in solution) and placing it into another container.

The term "selectively amplifying" refers to amplifying using one or more sequence-specific primers or primers that hybridize to adaptors that have been ligated to a product.

The term "ratio" refers to a molar ratio or relative concentration.

The term "ligatable ends" refers to a blunt end or an end that contains a 3' or 5' overhang that contains a 5' phosphate and/or a 3' hydroxyl that can be ligated to another nucleic acid molecule.

Alternative ligation reactions can be performed by Click chemistry (see, e.g., El-Sagheer et al J Am Chem Soc. 2009 131:3958-64) and GB1604559.3. In some cases, a terminal transferase can be used to ligate a triphosphate 5' base to a single-stranded DNA, which can be joined to another molecule.

The term "affinity tag" refers to a moiety that can tether a nucleic acid to a substrate. Biotin moieties (which term includes biotin and biotin analogues such as desthiobiotin, oxybiotin, 2'-iminobiotin, diaminobiotin, biotin sulfoxide, biocytin, etc., which bind to streptavidin) and chemoselective functional groups (e.g., an azide group or an alkyne group, which participate in click reactions) are examples of affinity tags.

The term "support" refers to a solid or semi-solid entity that contains a surface to which a nucleic acid can be tethered, e.g., a bead (e.g., a magnetic bead) or glass surface.

The term "tethering" means immobilizing to a surface of a support, covalently or non-covalently, directly or indirectly.

The term "separated" in the context of cleavage products that have been separated, refers to cleavage products that have been isolated from molecules that have not been cleaved.

The term "Argonaute" refers to a family of DNA-directed endonucleases represented by the Argonaute protein from *Natronobacterium gregoryi*. See, e.g., Gao et al Nat Biotechnol. 2016 34: 768-73.; Swarts et al Nature. 2014 507: 258-61; and Swarts et al. Nucleic Acids Res. 2015 43: 5120-9).

The term "CRISPR protein" refers to RNA-guided class 2 CRISPR-Cas endonuclease. This family includes Cas9, Cpf1, and others. See, e.g., Zetsche et al Cell 2015 163: 759-71 and Makarova Nat. Rev. Microbiol. 2015 13: 722-36.

DETAILED DESCRIPTION OF EXEMPLARY EMBODIMENTS

The present method may comprise reacting, i.e., digesting, a first sample comprising nucleic acid with a limiting amount of a first single-turnover sequence-specific endonuclease that recognizes a target sequence in the sample. Depending on the endonuclease used (e.g., whether the endonuclease is a homing endonuclease, a ribozyme, a DNAzyme or a nucleic acid-guided endonuclease such as an Argonaute or a CRISPR protein (e.g., Cpf1, Cas9 or a variant or ortholog thereof), the nucleic acid in the sample can be double-stranded DNA (e.g., genomic DNA or cDNA), single-stranded DNA or RNA. In some embodiments, the product in the sample may contain PCR products or pre-fragmented genomic DNA or a double-stranded amplification product of the same, to which adaptor sequences may or may not have been added. In some embodiments, the sample may be an adaptor tagged sequencing library. Each endonuclease molecule cleaves one strand or both strands at the target sequence. If the sample contains double-stranded DNA, then the endonuclease can cleave both strands at the target sequence. In some implementations, the endonuclease can cleave one strand at the target sequence to produce nicked nucleic acid. Because a limiting amount of the endonuclease is used, only a portion (i.e., some, but not all) of the nucleic acid molecules that comprise the target sequence are cleaved. Depending on the amount of nucleic acid in the sample, less than 50%, less than 30%, less than 20%, less than 10%, less than 5%, less than 2% or less than 1% of the molecules that contain the target sequence are cleaved. In these embodiments the amount of the cleavage product is determined by (i.e., should be directly proportional to) the limiting amount of the first single-turnover sequence-specific endonuclease used. As such, the amount of a first cleavage product produced should be known without needing to perform a quantification assay.

After the cleavage product has been produced, it may be isolated from non-cleaved nucleic acid, transcribed or selectively amplified. Examples of these reactions are described below.

The method may be used to normalize the amounts of particular molecules between two different samples (i.e., between at least a first sample and a second sample), such that the amount of cleavage product produced by the samples is approximately the same. In these embodiments, the method may comprise: (a) reacting a sample with a limiting amount of a single-turnover sequence-specific endonuclease that recognizes a target sequence, thereby cleaving a portion of the nucleic acid molecules that comprise the target sequence and producing a normalized amount of a first cleavage product; and (b) isolating, transcribing or selectively amplifying the normalized amount of the first cleavage product; and (c) reacting a second sample comprising nucleic acid with the limiting amount of the first single-turnover sequence-specific endonuclease (i.e., the same amount of the same endonuclease used in step (a) above), to cleave a portion of the nucleic acid molecules that comprise the target sequence. The portion of the nucleic acid molecules cleaved in this reaction may or not be the same as the portion of the nucleic acid molecules cleaved in step (a) above. However, because the amount of the cleavage product produced in this second reaction is determined by (i.e., should be directly proportional to) the limiting amount of the endonuclease used, the amount of the cleavage product produced should be approximately the same as the other (i.e., the first) reaction. In these embodiments, the amount of the second cleavage product is determined by the limiting amount of the first single-turnover sequence-specific endonuclease used in step (c), and the amount of the first cleavage product obtained from the first sample (in step (a) above) should be approximately the same as the normalized amount of the second cleavage product obtained from the second reaction of step (c). Again, after the cleavage product has been produced, it may be isolated from non-cleaved nucleic acid, transcribed or selectively amplified. Examples of these reactions are described below. This implementation of the method may be generally used to normalize a plurality of samples, so that the amount of material carried forward to the next step of the method should be the same for each sample and does not need to be measured.

In addition, the method may be used to normalize the amounts of two or more nucleic acid sequences (e.g., two or more different loci or PCR products) in the same sample. In these embodiments, the same sample may be reacted with a limiting amount of two or more single-turnover sequence-specific endonucleases, where each endonuclease targets a different sequence (e.g., a different locus or PCR product). Because the molar ratio of the products is determined by the amounts of the endonucleases used, the method may be used to produce mixes that contain pre-determined relative concentrations of two or more products. The products can be at any desired ratio, e.g., at an approximately 1:1 ratio. In these embodiments, step (c) may comprise reacting the first sample with a limiting amount of a second single-turnover sequence-specific endonuclease that recognizes a second target sequence (in addition to the first single-turnover sequence-specific endonuclease that recognizes the first target sequence, i.e., in the same reaction), thereby cleaving a portion of the nucleic acid molecules that comprise the second target sequence and producing a normalized amount of a second cleavage product in the same reaction as the first cleavage product. In this embodiment, the normalized amount of the first and second cleavage products in the reaction are determined by the limiting amounts of the first and second single-turnover sequence-specific endonucleases used. As would be apparent, the ratio of the normalized amount of the first cleavage product obtained from the first sample and the normalized amount of the second cleavage product obtained from the first sample is determined by the amounts of the first and second endonucleases used. As would be apparent, the method may comprise isolating, transcribing or selectively amplifying the normalized amount of the second cleavage product.

The normalized amount of the cleavage product can be isolated, transcribed or selectively amplified by any suitable method. For example, in some embodiments, the nucleic acid molecules in the sample of (a) may not have ligatable ends. For example, the nucleic acid may be an amplification product made using primers that do not have a 5' phosphate or may be treated to remove the 5' phosphate and/or the 3' hydroxyls. In these embodiments, reacting the sample with the single-turnover sequence-specific endonuclease produces a defined amount of cleavage product that comprises a ligatable end, i.e., an end that comprises a 5' phosphate and/or a 3' hydroxyl to which an adaptor can be ligated. In these embodiments, the method may comprise ligating an adaptor onto the cleavage product after cleavage but before it is isolated, transcribed or selectively amplified. In these embodiments, only the cleaved molecules are ligatable to the adaptor. The adaptor can be used to isolate, transcribe or selectively amplify the cleaved molecules. For example, in some embodiments the adaptor may comprise an affinity tag. In these embodiments, the method comprises separating the cleavage product from the remainder of the sample by binding the ligation products to a support that binds to the affinity tag. After the ligation products have been isolated, the isolated ligation product can itself be ligated to another adaptor (e.g., by fragmenting the isolated products and ligating it to adaptors, or by tagmentation). Alternatively, the adaptor may comprise a promoter sequence (e.g., a promoter for a bacteriophage polymerase such as T7 polymerase) and the method may comprise transcribing the cleavage product. In another embodiment, the adaptor may comprise a binding site for a primer and the method comprises copying the cleavage product by hybridizing a primer to the binding site and extending the primer using a template-dependent polymerase. This reaction may be done using a first primer that hybridizes to or has a 3' end that is the same as a sequence in the adaptor and a second primer that is gene specific. In this embodiment, the molecules that are ligated to the adaptor may be amplified by PCR, for example.

In an alternative embodiment that will be explained in greater detail below, the nucleic acid molecules in the sample may be attached to a support by one end. For example, the sample may contain PCR products that have been amplified using a pair of primers, wherein one of the primers has an affinity tag. The affinity tag can be used to tether the PCR products to a support. Alternatively, the sample could contain amplification products that were synthesized using primers that were tethered to a solid support, e.g., using bridge PCR or the like. In these embodiments, the endonuclease releases a normalized amount of the cleavage product from the support (i.e., into solution). The cleavage product can be readily isolated from the uncleaved molecules simply be transferring the solution phase of the reaction to a separate container. After the cleaved molecules are released and isolated, the method may comprise ligating an adaptor to the cleavage products. As noted above, this may be done by ligating an adaptor to the ends of the separated cleavage products (or fragments of the same) or by tagmenting the cleavage products.

In another embodiment, the cleaved products can be separated from the uncleaved products by a negative selection. In this embodiment, the endonuclease may cleave an end from a portion of the nucleic acid molecules. In this embodiment, step (b) may be done by removing the molecules that still contain the end by hybridization to a probe (e.g., a probe that is tethered to a support or a probe that contains an affinity tag that can bind to a support) that hybridizes to that end. Performing this step would leave the normalized amount of the first cleavage product in solution.

As would be apparent, the normalized amount of cleavage product can be input into a variety of different downstream methods. In some embodiments, the normalized amount of the cleavage product, or an amplification product thereof, may be sequenced. In these embodiments, the method may involve preparing a sequencing library, and then sequencing the library.

An embodiment of the method described generally above is described in greater detail below. This embodiment may comprise: (a) obtaining a sample comprising nucleic acid and (b) tethering at least some of the nucleic acid molecules in the sample to a support. The tethering may be done covalently (e.g., using click chemistry) or non-covalently using a biotin-streptavidin interaction. In this embodiment, the sample may comprise one or more double-stranded amplification products, e.g., PCR products. In this embodiment, the nucleic acid may be tethered to the support by an affinity tag that is in one of the primers used to amplify the sample. Alternatively, the nucleic acid in the sample may be synthesized in the presence of a relatively small amount of a biotynlyated nucleotide (e.g., biotin-dCTP), thereby allowing the molecules to be tethered to a support containing streptavidin. As with the method described above, next, the method comprises (c) reacting the tethered nucleic acid molecules produced by step (b) with a limiting amount of a first single-turnover sequence-specific endonuclease that recognizes a first target sequence in the sample, thereby cleaving a portion of the tethered nucleic acid molecules that comprise the target sequence and releasing a normalized amount of a first cleavage product into solution. Next, the method comprises (d) isolating the first cleavage product released in step (c). As would be apparent because the cleaved molecules are no longer tethered to the support, the isolation step may be conveniently done by transferring the liquid phase (the "supernatant") into another container. As described above, the amount of the first cleavage product isolated in step (d) is determined by the limiting amount of the first single-turnover sequence-specific endonuclease used in step (c).

As with the method generally described above, this embodiment of the method may be used to normalize the amounts of different nucleic acid species within a sample. As such, in some embodiment, step (c) of the method may comprise: (c) reacting the tethered nucleic acid molecules of (b) with: (i) a limiting amount of a first single-turnover sequence-specific endonuclease that recognizes a first target sequence in the sample, thereby cleaving a portion of the tethered nucleic acid molecules that comprise the target sequence and releasing a normalized amount of a first cleavage product into solution; and (ii) a limiting amount of a second single-turnover sequence-specific endonuclease that recognizes a second target sequence in the sample, thereby cleaving a portion of the tethered nucleic acid molecules that comprise the second target sequence and releasing a normalized amount of second cleavage product into solution; and (d) isolating the first and second cleavage products released in step (c); wherein the amounts of the first and cleavage products isolated in step (d) are determined by the limiting amounts of the first and second single-turnover sequence-specific endonucleases used in step (c). A would be apparent, two different nucleic acids can be normalized relative to one another in the same sample.

In this embodiment, the first endonuclease may cleave a first amplification product and the second endonuclease may cleave a sequence in a second amplification product. The target sequence may be in a primer (e.g., the primer used to tether the nucleic acid to the support) or it may be adjacent to the primers, e.g., at the end of the amplification products that is close to the primer that tethers the products to the support.

In these embodiments, the sample (which contains the first and second amplification products) may be made by producing the first and second amplification products in separate reactions (e.g., two different PCR reactions) and then pooling the products together. Alternatively, the first and second amplification products can be made in the same reaction, e.g., by multiplex PCR. Such a reaction may contain at least 2, at least 5, at least 10 amplification products, all of which can be normalized in a single reaction.

As with the method generally described above, this embodiment of the method may be used to normalize different samples (e.g., at least 10, at least 100 or at least 1000 samples). In these embodiments the method may further comprise: (e) obtaining a second sample comprising nucleic acid; (f) tethering at least some of the nucleic acid molecules in the second sample to a support; (g) reacting the tethered nucleic acid molecules of (f) with the same amount of the first single-turnover sequence-specific endonuclease as used in step (c) (i.e., the same amount of the same endonuclease), thereby cleaving a portion of the tethered nucleic acid molecules that comprise the target sequence and releasing a normalized amount of a second cleavage product into solution. The second cleavage product released in step (g) can then be isolated by transferring the solution phase to another container. As would be apparent, the amount of the second cleavage product released in step (g) is determined by the amount of the first single-turnover sequence-specific endonuclease used in step (g). In some embodiments, the amounts of the first and second cleavage products isolated in steps (c) and (g) are approximately the same.

After the products have been isolated, the method may comprise preparing a sequencing library from the released cleavage product. In some embodiments, this may comprise ligating an adaptor to the released cleavage product, or fragments of the same. This may be done by ligating an adaptor to the ends of the released cleavage product or by tagmenting the cleavage product. The adaptor-ligated cleavage products can then be optionally amplified and sequenced.

As would be apparent, the adaptors ligated to the fragments and/or the primers used for amplification may be compatible with use in a next generation sequencing platform, e.g., Illumina's reversible terminator method, Roche's pyrosequencing method (454), Life Technologies' sequencing by ligation (the SOLID platform), Life Technologies' Ion Torrent platform or Oxford Nanopore's MinIon system. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. The present method may be used on any sequencing platform, including those that are based on sequencing-by-synthesis (i.e., by extending a primer that is hybridized to a template).

Kits

Also provided by this disclosure is a kit for practicing the subject method, as described above. In some embodiments a kit may contain at least: a pair of primers for amplifying a product by PCR, wherein one of the primers comprises an affinity moiety; and a reprogrammed RNA-guided endonuclease that targets a sequence in the primer (in double-stranded form). In some embodiments, the kit may further comprise a support that binds to or reacts with the affinity moiety.

In addition, the kit may also comprise reagents for performing amplification (e.g., a polymerase, nucleotides and buffer, etc.), and other enzymes and/or reagents for performing the method, e.g., ligase, a primer, a support, etc. The various components of the kit may be present in separate containers or certain compatible components may be pre-combined into a single container, as desired.

In addition to the above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Embodiment

Embodiment 1. A method for processing a sample, comprising:

(a) reacting a first sample comprising nucleic acid with a limiting amount of a first single-turnover sequence-specific endonuclease that recognizes a target sequence, thereby cleaving a portion of the nucleic acid molecules that comprise the target sequence and producing a normalized amount of a first cleavage product; and (b) isolating, transcribing or selectively amplifying the normalized amount of the first cleavage product;

wherein the normalized amount of the first cleavage product is determined by the limiting amount of the first single-turnover sequence-specific endonuclease used in step (a).

Embodiment 2. The method of claim 1, further comprising:

(c) reacting a second sample comprising nucleic acid with the limiting amount of the first single-turnover sequence-specific endonuclease, thereby cleaving a portion of the nucleic acid molecules that comprise the target sequence and producing a normalized amount of a second cleavage product, (d) isolating, transcribing or selectively amplifying the normalized amount of the second cleavage product;

wherein the normalized amount of the second cleavage product is determined by the limiting amount of the first single-turnover sequence-specific endonuclease used in step (c); and wherein the normalized amount of the first cleavage product obtained from the first sample is approximately the same as the normalized amount of the second cleavage product obtained from the second sample.

Embodiment 3. The method of any prior embodiment, wherein step (c) further comprises: reacting the first sample with a limiting amount of second single-turnover sequence-specific endonuclease that recognizes a second target sequence, thereby cleaving a portion of the nucleic acid molecules that comprise the second target sequence and producing a normalized amount of a second cleavage product; and step (b) further comprises isolating, transcribing or selectively amplifying the normalized amount of the first cleavage product;

wherein the normalized amount of the second cleavage product is determined by the limiting amount of the second single-turnover sequence-specific endonuclease used in step (c); and wherein the ratio of the normalized amount of the first cleavage product obtained from the first sample and the normalized amount of the second cleavage product obtained from the first sample is determined by the amounts of the first and second endonucleases used.

Embodiment 4. The method of any prior embodiment, wherein:

the nucleic acid molecules in the sample of (a) do not have ligatable ends;

reacting the sample with the single-turnover sequence-specific endonuclease produces a defined amount of cleavage product that comprise a ligatable end; and the method comprises ligating an adaptor onto the cleavage product between steps (a) and (b).

Embodiment 5. The method of embodiment 4, wherein the adaptor comprises an affinity tag and the method comprises separating the cleavage product from the remainder of the sample by binding to a support that binds to the affinity tag.

Embodiment 6. The method of embodiment 5, further comprising ligating an adaptor to the separated cleavage products.

Embodiment 7. The method of embodiment 6, wherein the ligating is done by ligating an adaptor to the ends of the separated cleavage products or by tagmenting the cleavage products.

Embodiment 8. The method of embodiment 4, wherein the adaptor comprises an RNA promoter sequence and the method comprises transcribing the cleavage product.

Embodiment 9. The method of embodiment 4, wherein the adaptor comprises a binding site for a primer and the method comprises copying the cleavage product by hybridizing a primer to the binding site and extending the primer using a template-dependent polymerase.

Embodiment 10. The method of any prior embodiment, wherein: i. the nucleic acid molecules in the sample are attached to a support by one end only, ii. the endonuclease releases the normalized amount of the cleavage product into solution, and iii. the method comprises isolating the released cleavage product.

Embodiment 11. The method of embodiment 10, further comprising ligating an adaptor to the released cleavage products.

Embodiment 12. The method of embodiment 11, wherein the ligating is done by ligating an adaptor to the ends of the separated cleavage products or by tagmenting the cleavage products.

Embodiment 13. The method of any prior embodiment, wherein the endonuclease cleaves an end from a portion of the nucleic acid molecules, and step (b) is done by removing the molecules that still contain the end by hybridization to surface-tethered probe that hybridizes to the end, thereby leaving the normalized amount of the first cleavage product in solution.

Embodiment 14. The method of any prior embodiment, further comprising sequencing the normalized amount of the first cleavage product, or an amplification product thereof.

Embodiment 15. The method of any prior embodiment, wherein the single-turnover sequence-specific endonuclease is a homing endonuclease, a ribozyme, a DNAzyme or a nucleic acid-guided endonuclease.

Embodiment 16. The method of embodiment 15, wherein the single-turnover sequence-specific endonuclease is Argonaute or CRISPR protein.

Embodiment 17. The method of embodiment 16, wherein the CRISPR protein is Cpf1, Cas9 or a variant or ortholog thereof.

Embodiment 18. The method of any prior embodiment, wherein the nucleic acid in the sample is a double-stranded amplification product.

Embodiment 19. The method of embodiment 18, wherein the nucleic acid in the sample is a product of a polymerase chain reaction (PCR).

Embodiment 20. The method of any prior embodiment, wherein the nucleic acid in the sample has been enriched from an initial sample.

Embodiment 21. A method for processing a sample, comprising:
(a) obtaining a sample comprising nucleic acid;
(b) tethering at least some of the nucleic acid molecules in the sample to a support (e.g., by one end and not the other);
(c) reacting the tethered nucleic acid molecules of (b) with a limiting amount of a first single-turnover sequence-specific endonuclease that recognizes a first target sequence in the sample, thereby cleaving a portion of the tethered nucleic acid molecules that comprise the target sequence and releasing a normalized amount of a first cleavage product into solution, and
(d) isolating the first cleavage product released in step (c);
wherein the amount of the first cleavage product isolated in step (d) is determined by the limiting amount of the first single-turnover sequence-specific endonuclease used in step (c).

Embodiment 22. The method of embodiment 21, wherein the nucleic acid in the sample is an amplification product.

Embodiment 23. The method of embodiment 21, wherein the amplification product comprises PCR products.

Embodiment 24. The method of any of embodiments 21-23, wherein step (c) of the method comprises:
(c) reacting the tethered nucleic acid molecules of (b) with:
(i) a limiting amount of a first single-turnover sequence-specific endonuclease that recognizes a first target sequence in the sample, thereby cleaving a portion of the tethered nucleic acid molecules that comprise the target sequence and releasing a normalized amount of a first cleavage product into solution; and
(ii) a limiting amount of a second single-turnover sequence-specific endonuclease that recognizes a second target sequence in the sample, thereby cleaving a portion of the tethered nucleic acid molecules that comprise the second target sequence and releasing a normalized amount of second cleavage product into solution; and
(d) isolating the first and second cleavage products released in step (c);
wherein the amounts of the first and cleavage products isolated in step (d) are determined by the limiting amounts of the first and second single-turnover sequence-specific endonucleases used in step (c).

Embodiment 25. The method of any of embodiments 21-24, wherein the first endonuclease cleaves a first amplification product and the second endonuclease cleaves a sequence in a second amplification product.

Embodiment 26. The method of embodiment 25, wherein the first and second amplification products made in separate reactions and then pooled together.

Embodiment 27. The method of embodiment 25, wherein the first and second amplification products are made in the same reaction.

Embodiment 28. The method of any of embodiments 21-27, wherein the method further comprises:
(e) obtaining a second sample comprising nucleic acid;
(f) tethering at least some of the nucleic acid molecules in the second sample to a support;
(g) reacting the tethered nucleic acid molecules of (f) with the same amount of the first single-turnover sequence-specific endonuclease as used in step (c), thereby cleaving a portion of the tethered nucleic acid molecules that comprise the target sequence and releasing a normalized amount of a second cleavage product into solution; and
(h) isolating the second cleavage product released in step (g);
wherein the amount of the second cleavage product released in step (g) is determined by the amount of the first single-turnover sequence-specific endonuclease used in step (g), and wherein the amounts of the first and second cleavage products isolated in steps (d) and (h) are approximately the same.

Embodiment 29. The method of any of embodiments 21-28, further comprising preparing a sequencing library from the released cleavage product.

Embodiment 30. The method of any of embodiments 21-29, further comprising ligating an adaptor to the released cleavage product.

Embodiment 31. The method of embodiment 30, wherein the ligating is done by ligating an adaptor to the ends of the released cleavage product or by tagmenting the cleavage product.

Embodiment 32. The method of any of embodiments 21-31, further comprising sequencing the released cleavage product.

Embodiment 33. The method of any of embodiments 21-32, further comprising amplifying the released cleavage product.

Embodiment 34. The method of any of embodiments 21-33, wherein the nucleic acid in the sample has been enriched from an initial sample.

Embodiment 35. The method of any of embodiments 21-34, wherein the nucleic acid molecules are tethered to the support by a covalent bond.

Embodiment 36. The method of embodiment 35, wherein the tethering is done using click chemistry.

Embodiment 37. The method of any of embodiments 21-36, wherein the nucleic acid molecules are tethered to the support by a non-covalent bond.

Embodiment 38. The method of embodiment 17, wherein the tethering is done via a biotin/streptavidin interaction.

Embodiment 39. A kit comprising:
a pair of primers for amplifying a product by PCR, wherein one of the primers comprises an affinity moiety; and
a reprogrammed RNA-guided endonuclease that targets a sequence in the primer, in double-stranded form.

Embodiment 40. The kit of embodiment 39, further comprising a support that binds to or reacts with the affinity moiety.

EXAMPLE

The following example is provided in order to demonstrate and further illustrate certain embodiments and aspects of the present invention and are not to be construed as limiting the scope thereof. In many protocols the reactions are cleaned up by beads or a column (e.g., AM Pure XP beads), the amount of nucleic in the sample is quantified (e.g., using a Qubit assay) and a given volume of reaction used in downstream steps. Such protocols, while they are relatively inexpensive and easy to perform and require relatively inexpensive capital equipment (e.g., a fluorometer), do require a number of hands on steps and calculations. User error is therefore a real concern. The steps could potentially be automated but this depends on the sophistication of the laboratory in which assays are performed.

Described here is an alternative approach to normalize on-target DNA, and even individual amplicons within a sample (e.g. in a multiplex PCR reaction). The approach described below uses the Cas9 nuclease. However, any sequence-specific single-turnover endonuclease (e.g., homing endonucleases, ribozymes, DNAzymes or other CRISPR endonucleases such as Cpf1 and Argonaute) could potentially be used. A Cas9-RNA complex forms a double-stranded endonuclease, targeted by sequence complementarity between the RNA and target sequence. Whilst mostly described for in vivo editing, Cas9 can also be used in vitro.

The most important property of the Cas9 nuclease, in terms of the present method, is that it is a single turnover enzyme (Sternberg et al 2014 Nature 507: 62-67). This means that one Cas9-RNA complex cleaves exactly one DNA molecule (and no more). If target DNA is in excess, and the reaction allowed to continue ad infinitum, the number of cleaved DNA molecules is equal to the number of Cas9-RNA complexes. In many reaction conditions, equilibrium can be reached after about 1 minute; the cleaved DNA does not increase with further incubation time (Sternberg et al, supra).

Figure 1:
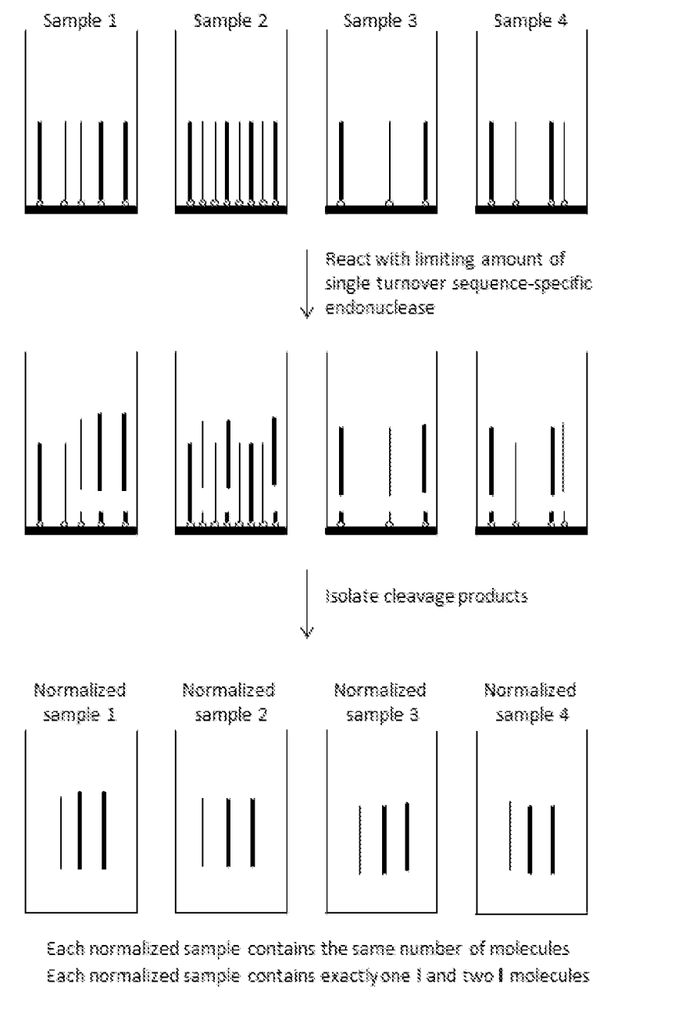

This property (i.e., the single turnover property) of Cas9-RNA can be used to normalize a sample. An example of such a method is shown in FIG. 1. In this example, PCR amplicons are immobilized to a solid surface and then washed to remove unbound material. A defined amount of Cas9-RNA is then added ensuring that template DNA is in excess. Cleavage by Cas9-RNA depends on the guide RNA sequence. Guide RNAs can be designed to cleave all of the desired amplification products via a common sequence. In some cases, guide RNAs can be designed to cleave specific amplicons in desired ratios (for example, when one wants to recover more molecules of one amplicon because it is difficult to process in downstream steps). The second approach may use a pool of guide RNAs at known concentrations. However the digestion is performed, the result is that a specific number of amplicon molecules are cleaved. The digested amplicons can then be isolated from the supernatant. The amplicons can then be processed individually in future steps or pooled and then processed.

The Cas9-RNA complex should dissociate from the ends of the cleaved target because the target sequence (i.e., the target sequence targeted by the guide RNA is cut in the target). If Cas9-RNA fails to dissociate from the target (and the Cas9-RNA complex binding site is required for the next step of the method), the guide RNA could be hydrolyzed (e.g., via alkaline hydrolysis or an RNAse), the complex could be disassociated by heat, or the Cas9 protein could be digested by a protease. Alternative methods are known and could be employed if necessary. For example, one could use detergents such as sodium dodecyl sulfate or reducing agents such as dithiothreitol or 2-mercaptoethanol to denature proteins.

In some cases, the method could be implemented by (1) pooling all reactions, (2) using a pool of Cas9-RNAs to normalize different samples (based on e.g. sample specific sequences which could be included in addition to sample identifier barcodes that can be used in subsequent sequence analysis).

Cas9-RNA could also be used for target enrichment. For example, a pool of DNA molecules e.g. a genomic DNA sample could be immobilized and then specific targets digested by a pool of Cas9-RNAs and released into the supernatant. The digested products would also have blunt ends with known sequences. These could be used for downstream steps.

Example 1

Template Amplification and Normalization Method

The final concentrations of components in a standard 30 µL protocol are 3 nM dsDNA template, 30 nM Cas9, and 30 nM guide RNA. To drive the standard reaction, the Cas9-RNA is present at a 10-fold excess. Instead of a Cas9:RNA:dsDNA ratio of 10:10:1 the ratios are modified to be, e.g., 1:1:≥10 to limit digestion according to the total number of Cas9-RNA molecules.

In this example, 1.5 ng of a total PCR amplicon is used in the next step of the method (or "taken forward"), which sets the minimum dsDNA that could be released from a solid surface. Given a mean amplicon size of about 800 bp, 1.5 ng dsDNA is about 0.003 pmol. If 1.5 ng dsDNA is digested then one may need to remove 100% of the supernatant. This is not optimal because one may wish to carry forward less of the reaction (e.g., to aid with buffer compatibility with the next steps in the workflow) and allow some dead volume. If 10% of the supernatant is taken forward, then one would need to release a total of 15 ng or 0.03 pmol dsDNA.

The following calculations assume a 10 µL final reaction volume (and removal of 1 µL for use in subsequent reactions). If one wants to release a total of 0.03 pmol dsDNA then a total of 0.03 pmol Cas9 and 0.03 pmol RNA can be used. If one assumes a 10-fold excess of dsDNA template then 0.3 pmol dsDNA template can be used. The final reaction concentrations in a 10 µL final reaction volume are therefore dsDNA 0.03 pmol/µL (30 nM), Cas9 0.003 pmol (3 nM) and RNA 0.003 pmol (3 nM).

The volume of the PCR reaction incubated with the support (e.g., beads) can exceed the Cas9-RNA reaction volume. There is a washing step after bead binding, after which beads can be resuspended in a lower volume. If one incubates beads with 50 µL of a PCR product and assumes that binding is 100% efficient, then the concentration of an 800 bp amplicon (for example) may exceed 3 ng/µL. Binding smaller volumes of a PCR reaction assumes a higher concentration of products from the PCR. For example, in this example, incubating 10 µL of a PCR product assumes that the product has a concentration of greater than 15 ng/µL. The overall mass needed can be further limited if a greater proportion of digested product is removed from the supernatant. For example, if 20%, instead of 10% of the supernatant taken forward into the next steps then the mass requirements are halved.

NEB and other vendors currently supply Cas9 at a concentration of 1 µM (1 pmol/µL). If one adds 1 µL of Cas9 to the 10 µL final reaction then one may need to dilute Cas9 to a concentration of 0.03 pmol/µL (30 nM). Similarly, adding 1 µL of RNA to a 10 µL final reaction may require an RNA stock concentration of 0.03 pmol/µL (30 nM). 1 mg of Bangs Laboratories Nuclease-free beads will bind 25 pmol of a 1 kb 5' biotinylated dsDNA. The above calculations assume that one needs to bind at least 0.3 pmol dsDNA template. 0.012 mg beads may therefore be used for each reaction. Beads are at a concentration of 1 mg/mL therefore one may use 12 µLs beads per reaction.

The following workflow assumes 48× samples and provides mastermixes that have about 10% extra volume. The binding protocol described below is adapted from Product Data Sheet for 530 BioMag® Streptavidin, Nuclease-free, from Bangs Laboratories:

1. Dispense 640 µL beads into a nuclease-free 1.5 mL microcentrifuge tube. Using a magnetic separation unit, pull the magnetic particles to the side of the microcentrifuge tube for 30 seconds. Remove and discard the supernatant. Resuspend the beads in 320 µL of binding buffer (20 mM Tris, 0.5 M NaCl at pH 8.0).

2. Aliquot 6 µL of beads into each well of a 96-well plate.

3. Add 10 µL biotinylated PCR amplicon directly to each well of the 96-well plate. Incubate at room temperature for 15 min.

4. While the biotinylated PCR amplicon is binding at room temperature make up the following mix and pre-incubate at 37° C. for at least 10 mins.

| Component | µL | Final Concentration |
|---|---|---|
| Water | 7 | |
| 10× reaction buffer | 1 | 1× |
| 30 nM gRNA | 1 | 3 nM |
| 30 nM Cas9 nuclease | 1 | 3 nM |

5. Magnetically separate beads for 30 seconds and discard the supernatant. Wash the bound particles with 50 µL of binding buffer 2 times leaving the magnetic particles as a wet cake.

6. Add the 10 µL reaction components from step 4 to the beads. Use the following thermocycling program: 37° C. 60 mins, 65° C. for 20 mins, 4° C. store. The 65° C. heat inactivation is designed to release Cas9-RNA from DNA.

7. Remove 1 µL of the supernatant into a new 96-well plate. The plate now contains normalized library.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. A method for normalizing a sample, comprising:
   (a) obtaining a sample comprising nucleic acid;
   (b) tethering at least some of the nucleic acid molecules in the sample to a support;
   (c) reacting the tethered nucleic acid molecules of (b) with a limiting amount of a first Cas9-RNA complex that recognizes a first target sequence in the sample, thereby cleaving a portion of the tethered nucleic acid molecules that comprise the first target sequence and releasing a normalized amount of a first cleavage product into solution, and
   (d) isolating the first cleavage product released in step (c);
   wherein the amount of the first cleavage product isolated in step (d) is determined by the limiting amount of the Cas9-RNA complex used in step (c).

2. The method of claim 1, wherein the nucleic acid in the sample is an amplification product.

3. The method of claim 1, wherein the amplification product comprises PCR products.

4. The method of claim 1, wherein step (c) of the method comprises:
   (c) reacting the tethered nucleic acid molecules of (b) with:
      (i) a limiting amount of a first Cas9-RNA complex that recognizes a first target sequence in the sample, thereby cleaving a portion of the tethered nucleic acid molecules that comprise the first target sequence and releasing a normalized amount of a first cleavage product into solution; and
      (ii) a limiting amount of a second Cas9-RNA complex that recognizes a second target sequence in the sample, thereby cleaving a portion of the tethered nucleic acid molecules that comprise the second target sequence and releasing a normalized amount of second cleavage product into solution; and
   step (d) comprises:
   (d) isolating the first and second cleavage products released in step (c);
   wherein the amounts of the first and second cleavage products isolated in step (d) are determined by the limiting amounts of the first and second Cas9-RNA complexes used in step (c).

5. The method of claim 4, wherein the first Cas9-RNA complex cleaves a first amplification product and the second Cas9-RNA complex cleaves a sequence in a second amplification product.

6. The method of claim 5, wherein the first and second amplification products are made in separate reactions and then pooled together.

7. The method of claim 5, wherein the first and second amplification products are made in the same reaction.

8. The method of claim 1, wherein the method further comprising:
   (e) obtaining a second sample comprising nucleic acid;
   (f) tethering at least some of the nucleic acid molecules in the second sample to a support;
   (g) reacting the tethered nucleic acid molecules of (f) with the same amount of the first Cas9-RNA complex as used in step (c), thereby cleaving a portion of the tethered nucleic acid molecules that comprise the target sequence and releasing a normalized amount of a second cleavage product into solution; and
   (h) isolating the second cleavage product released in step (g);
   wherein the amount of the second cleavage product released in step (g) is determined by the amount of the first Cas9-RNA complex used in step (g), and wherein the amounts of the first and second cleavage products isolated in steps (d) and (h) are approximately the same.

9. The method of claim 1, further comprising preparing a sequencing library from the released cleavage product.

10. The method of claim 1, further comprising ligating an adaptor to the released cleavage product.

11. The method of claim 10, wherein the ligating is done by ligating an adaptor to the ends of the released cleavage product or by tagmenting the cleavage product.

12. The method of claim 1, further comprising sequencing the released cleavage product.

13. The method of claim 1, further comprising amplifying the released cleavage product.

14. The method of claim 1, wherein the nucleic acid in the sample has been enriched from an initial sample.

15. The method of claim 1, wherein the nucleic acid molecules are tethered to the support by a covalent bond.

16. The method of claim 15, wherein the tethering is done using click chemistry.

17. The method of claim 1, wherein the nucleic acid molecules are tethered to the support by a non-covalent bond.

18. The method of claim 17, wherein the tethering is done using a biotin/streptavidin interaction.

19. A kit comprising:
- a pair of primers for amplifying a product by PCR, wherein one of the primers comprises an affinity moiety; and
- a Cas9-RNA complex that targets a sequence in the primer, in double-stranded form.

20. The kit of claim 19, further comprising a support that binds to or reacts with the affinity moiety.

* * * * *